US008090446B2

(12) United States Patent
Fowler et al.

(10) Patent No.: US 8,090,446 B2
(45) Date of Patent: Jan. 3, 2012

(54) METHODS AND SYSTEMS FOR ESTABLISHING NEURAL STIMULATION PARAMETERS AND PROVIDING NEURAL STIMULATION

(75) Inventors: Brad Fowler, Duvall, WA (US); Justin Hulvershorn, Seattle, WA (US); Bradford E. Gliner, Sammamish, WA (US); Leif R. Sloan, Seattle, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 784 days.

(21) Appl. No.: 12/099,415

(22) Filed: Apr. 8, 2008

(65) Prior Publication Data
US 2009/0099622 A1    Apr. 16, 2009

Related U.S. Application Data

(60) Provisional application No. 60/912,911, filed on Apr. 19, 2007.

(51) Int. Cl.
*A61N 1/36* (2006.01)
(52) U.S. Cl. ............................................ 607/45; 607/46
(58) Field of Classification Search .................... 607/45, 607/46
See application file for complete search history.

(56) References Cited

U.S. PATENT DOCUMENTS

| 5,458,117 A * | 10/1995 | Chamoun et al. ............. 600/547 |
| 2004/0034394 A1 * | 2/2004 | Woods et al. .................... 607/46 |
| 2004/0176831 A1 | 9/2004 | Gliner et al. |
| 2004/0215288 A1 | 10/2004 | Lee et al. |
| 2005/0070971 A1 * | 3/2005 | Fowler et al. ................... 607/45 |
| 2006/0015153 A1 | 1/2006 | Gliner et al. |
| 2007/0032834 A1 | 2/2007 | Gliner et al. |

FOREIGN PATENT DOCUMENTS

WO    WO 03/066158    8/2003

OTHER PUBLICATIONS

International Search Report and Written Opinion for PCT/US2008059645; Applicant: Northstar Neurscience, Inc.; dated Jul. 17, 2008; 16 pgs.

* cited by examiner

*Primary Examiner* — Scott Getzow
*Assistant Examiner* — Joseph Dietrich
(74) *Attorney, Agent, or Firm* — Melissa Acosta; Christopher S. L. Crawford; Craig Hoersten

(57) ABSTRACT

Methods for providing electrical stimulation therapy to a cortex of a patient via a plurality of electrodes proximate to the cortex and a pulse generator implanted in the patient. One embodiment of a method in accordance with the invention comprises determining whether the current applied via the plurality of electrodes results in a sufficient current density in the cortex. The current density, for example, may need to be high enough to induce a response in the patient for determining the activation threshold of the specific stimulation site, or the current density may need to be high enough to perform a specific therapy. If the current density is not sufficient, the method continues by selecting a subset of the plurality of electrodes, and applying electrical current to the cortex via the subset of the electrodes. For example, if the current density is not sufficient when the current is applied to the full plurality of electrodes at approximately the maximum output of the pulse generator, then the current level from the pulse generator can be applied to only a subset of the electrodes to effectively increase the current density in the cortex at the active electrodes.

25 Claims, 10 Drawing Sheets

METHODS AND SYSTEMS FOR ESTABLISHING NEURAL STIMULATION PARAMETERS AND PROVIDING NEURAL STIMULATION

CROSS-REFERENCE TO RELATED APPLICATION

This application claims benefit of U.S. Provisional Application No. 60/912,911, filed Apr. 19, 2007, which is incorporated herein in its entirety.

TECHNICAL FIELD

The present invention is directed generally toward methods and systems for establishing neural stimulation parameters and/or applying neural stimulation at desired signal intensities, densities, or distributions in view of an output signal limitation or target signal level associated with a power source such as a pulse generator.

BACKGROUND

A wide variety of mental and physical processes are controlled or influenced by neural activity in particular regions of the brain. In some areas of the brain, such as in the sensory or motor cortices, the organization of the brain resembles a map of the human body; this is referred to as the "somatotopic organization of the brain." There are several other areas of the brain that appear to have distinct functions that are located in specific regions of the brain in most individuals. In the majority of people, for example, areas of the occipital lobes relate to vision, regions of the left inferior frontal lobes relate to language, and regions of the cerebral cortex appear to be consistently involved with conscious awareness, memory, and intellect. This type of location-specific functional organization of the brain, in which discrete locations of the brain are statistically likely to control particular mental or physical functions in normal individuals, is herein referred to as the "functional organization of the brain."

Many problems or abnormalities can be caused by damage from disease and/or disorders of the brain. A stroke, for example, is one common condition that damages the brain. Strokes are generally caused by emboli (e.g., obstruction of a vessel), hemorrhages (e.g., rupture of a vessel), or thrombi (clotting) in the vascular system of a specific region of the cortex, which in turn generally causes a loss or impairment of neural function (e.g., neural functions related to face muscles, limbs, speech, etc.). Other problems or abnormalities can be caused by traumatic brain injury, memory diseases/disorders (e.g., Alzheimer's, dementia, etc.), movement disorders, tinnitus, neuropsychiatric and/or neurocognitive disorders, addictions, and/or other conditions.

Several existing techniques for treating various conditions involve electrically stimulating certain regions of the brain. In stroke cases, for example, Northstar Neuroscience, Inc., has pioneered electrically stimulating selected regions of the cortex to treat stroke-related conditions. Northstar Neuroscience has discovered that stimulating selected areas of the cortex below the activation threshold of a population of neurons at the stimulation site is beneficial in treating such conditions. For example, the activation threshold can be the minimum electrical current that triggers a motor response or a sensation, and the therapeutic electrical current can be applied at approximately 50% or another subthreshold level of the movement or sensation current. Therefore, it is useful to first determine the electrical current that induces a movement and/or sensory response at the stimulation site to effectively conduct subthreshold stimulation therapies.

One challenge of conducting subthreshold stimulation therapies is determining the activation threshold for the stimulation site. As mentioned above, the therapy level can be based on the minimum level of current that induces movement in the patient's affected body part and/or a sensation perceived by the patient. The minimum activation current level is generally determined by applying the stimulation at increasing current or voltage levels until the stimulation itself evokes a movement, a sensation, and/or another type of measurable response in the patient. The implantable pulse generators, however, have only a limited output capacity that in certain situations may not be sufficient to evoke such a response. When this occurs, it is difficult to estimate the minimum activation current, and thus the stimulation may not be applied in a desired subthreshold stimulation range.

Another aspect of applying electrical stimulation to the cortex is to provide a sufficient current over a desired area of the cortex to achieve an intended effect and/or drive the electrical signal to a desired depth within the cortex. For example, it may be advantageous to stimulate an area that covers portions of the sensory cortex, motor cortex, and/or pre-motor cortex. This generally requires an electrode array with a plurality of contacts (e.g., a 2×3 electrode array). This can also require a higher current level to achieve an intended effect. Such a current level may exceed the maximum output of the implantable pulse generator. As a result, the implantable pulse generator may not be adequate for performing certain therapies.

DETAILED DESCRIPTION

A. Overview

Figure 1A:
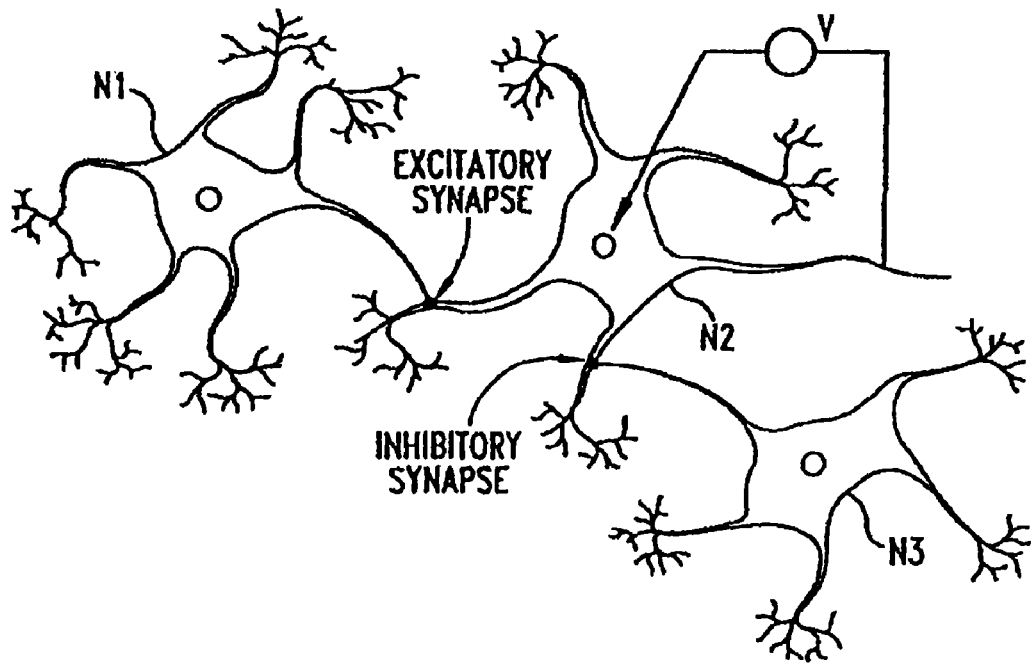
FIG. 1A is a schematic view of neurons.

The following description sets forth several embodiments and methods for providing electromagnetic signals (e.g., stimulation) to a cortical and/or other region of a patient. Several embodiments described below make reference to stimulation, which, as used herein, can refer to signals that provide an inhibitory or facilitatory effect on a target neural population, depending on factors including, but not limited to, the location of the target area and the signal delivery parameters. In various embodiments, the electromagnetic stimulation involves electrical signals that are applied via a plurality of electrodes proximate to the cortex and a pulse generator implanted in the patient. One embodiment of a method in accordance with the invention comprises determining whether a signal applied or directed to a target neural population results in a sufficient signal intensity, density, distribution, and/or duration applied or delivered (epidurally or subdurally) to the cortex. The sufficiency of any given signal intensity may be indicated or estimated by an extent to which the applied signal a) evokes, induces, causes, or correlates with a particular type of patient response or effect associated with the neural function of the target neural population to which the signal is applied; and/or b) produces or leads to an intended therapeutic effect. The signal intensity at any given time may correspond to or vary in accordance with a particular set of signal parameters, such as a current level; a voltage level; a pulse width; a signal polarity; a pulse or burst pattern; a spatial signal application pattern or distribution; and/or a temporal signal application pattern or sequence.

For ease of understanding, in various embodiments described herein, a current level, a spatial electrode activation configuration and/or a temporal electrode activation sequence may be varied to affect current density, thereby affecting signal intensity. Additionally or alternatively, in certain embodiments, a pulse width or signal duration may be varied to affect signal intensity. Those of ordinary skill in the art will understand that in these or other embodiments, one or more other parameters (e.g., a voltage level) could be varied to affect signal intensity.

In one method, the current density, for example, may need to be high enough to induce a response in the patient for determining a neural activation threshold associated with a specific stimulation site, or the current density may need to be high enough to perform a specific therapy. If the current density is not sufficient, the method continues by selecting a subset of the plurality of electrodes, and applying electrical current to the cortex via the subset of the electrodes. For example, if the current density is not sufficient when the current is applied to the full or an initial plurality of electrodes at a hardware or software based upper current limit or approximately the maximum output of the pulse generator, then current from the pulse generator can be applied to only a subset of the electrodes to effectively increase the current density applied to the cortex proximate to the active electrodes.

Another embodiment of a method in accordance with the invention is directed toward determining a stimulation current or current density to be delivered to the cortex of a patient during therapy. One embodiment of this method includes applying electrical current to the cortex via a plurality of electrodes up to approximately the maximum output of an implanted pulse generator without triggering a motor, sensory, or other response or effect in the patient. This embodiment of the method continues by selecting at least one subset of the plurality of electrodes, applying electrical current to the cortex via the subset of electrodes at a current level that triggers a response in the patient (e.g., a threshold or suprathreshold current), and selecting a subthreshold stimulation current density less than the suprathreshold current density that triggered the response in the patient.

Another method in accordance with the invention is directed toward applying an electrical signal to a cortex to a patient via a pulse generator implanted in the patient. An embodiment of this method includes implanting an electrode array at least proximate to the cortex of the patient. The electrode array has a plurality of electrodes mounted to a support member, which may be flexible. The electrodes, for example, can have at least a first subset with at least one first electrode and a second subset with at least one second electrode. The electrode array is also electrically coupled to the implanted pulse generator such that at least one first electrode can be operated independently of at least one second electrode. In one embodiment, the method continues by determining whether a base current density associated with an initial electrode configuration and/or cortical area is sufficient to carry out an aspect of a cortical stimulation therapy for the patient when an upper signal limit or approximately the maximum output of the pulse generator is applied concurrently to the first electrode(s) and the second electrode(s). The method further includes applying a first electrical current to the cortex via the first electrode(s) for a first time period without applying electrical stimulation to the second electrode(s) such that a first current density provided by the first electrode(s) is higher than the base current density. The method can also include applying a second electrical current to the cortex via the second electrode(s) for a second time period without applying electrical stimulation to the first electrode(s) or in association with applying a reduced level of stimulation to the first electrode(s), such that a second current density provided by the second electrode(s) is higher than the base current density. Depending upon embodiment details, the first and second electrical currents may be identical, essentially identical, or different; and the first and second time periods may be identical, essentially identical, or different.

FIGS. 1A-6 set forth specific details of several embodiments of the inventive methods to provide a thorough understanding of these embodiments. Several details describing well-known structures often associated with implanted pulse generators, electrode arrays or other aspects of providing electrical stimulation to the brain are not set forth in the following description to avoid unnecessarily obscuring the description of the disclosed embodiments. Additionally, several other embodiments of the invention can have different configurations, procedures or components than those described in this section. As such, a person of ordinary skill in the art will accordingly understand that the invention may have other embodiments with additional elements or without several of the elements shown and described below with reference to FIGS. 1A-6.

B. Embodiments of Providing Electrical Stimulation to the Cortex

Figure 1B:
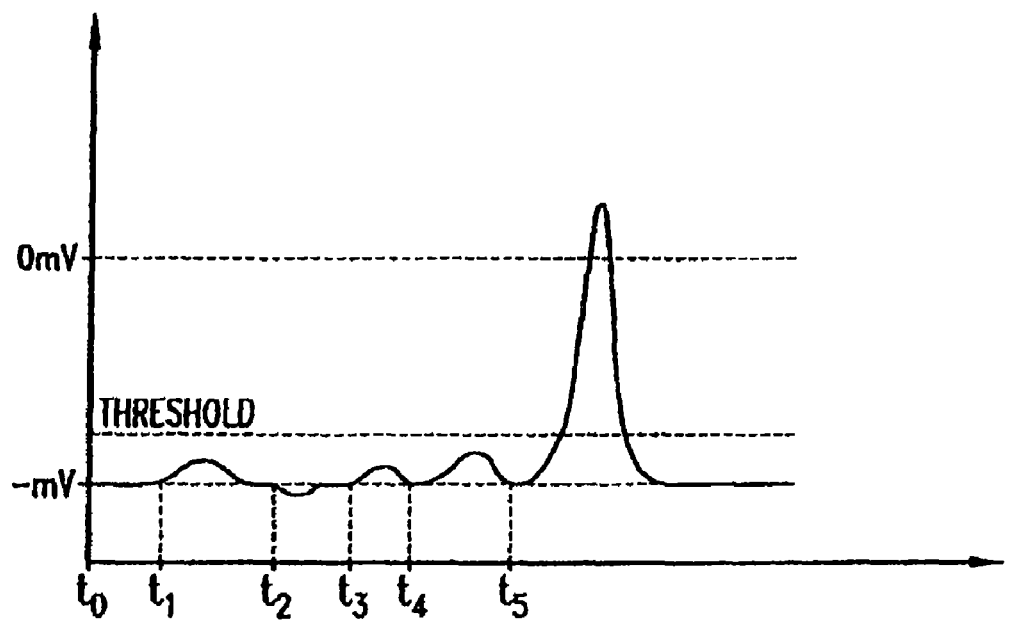
FIG. 1B is a graph illustrating firing an action potential associated with normal neural activity.

FIG. 1A is a schematic representation of several neurons N1-N3, and FIG. 1B is a graph illustrating an "action potential" related to neural activity in a normal neuron. Neural activity is governed by electrical impulses generated in neurons. For example, neuron N1 can send excitatory inputs to neuron N2 (e.g., at times $t_1$, $t_3$ and $t_4$ in FIG. 1B), and neuron N3 can send inhibitory inputs to neuron N2 (e.g., at time $t_2$ in FIG. 1B). The neurons receive/send excitatory and inhibitory inputs from/to a population of other neurons. Within a given neuron, an integration of the excitatory and inhibitory inputs can produce "action potentials" in the neuron, which are electrical pulses that propagate by changing the flux of sodium (Na) and potassium (K) ions across the cell membrane. An action potential occurs when an integration of neural input signals surpasses a threshold level. When this threshold level is reached, an "all-or-nothing" action potential is generated. For example, as shown in FIG. 1B, the excitatory input at time $t_5$ causes neuron N2 to "fire" an action potential because the input exceeds the threshold level for generating the action potential. The action potentials propagate down the length of the axon (the long portion of the neuron that makes up nerves or neuronal tracts) to cause the release of neurotransmitters from that neuron, which will further influence adjacent neurons.

In various instances, it may be desirable to electrically stimulate neurons at subthreshold levels. For example, it may be desirable to provide stimulation to motor, sensory and/or other neurons at subthreshold levels, and then rely on the (perhaps limited) ability of neurons to intrinsically supplement the stimulation signal. The combination of the external electromagnetic stimulation and the neuron's internal or intrinsic ability to generate at least some dendritic depolarization waves and/or an increase in neural potential can be sufficient to result in a summation or integration of neural input signals that exceeds the threshold level and generates a set of action potentials. In such instances, it can be important to determine, or at least approximately determine or otherwise estimate, a threshold potential for a given neural population. Otherwise, the target neurons may be overstimulated, or the neurons may not receive a therapeutically relevant or useful dose of stimulation (e.g., if the stimulation is provided outside of a particular stimulation parameter range). In particular instances, however, it may be desirable to briefly stimulate neurons with near threshold, threshold, and/or suprathreshold pulses or bursts instead of and/or in association with subthreshold stimulation.

In the case of motor or sensory neurons, a threshold level can generally be determined by varying a stimulation parameter (e.g., increasing a voltage, current, pulse width, and/or frequency of the stimulation signal) until a motor response or a sensory response is detected. A motor response can often be detected by simply observing or measuring (e.g., using electromyography (EMG)) muscle action exhibited by the patient. In a generally similar manner, particular sensory neurons can be stimulated and a threshold for such neurons can be detected when the patient receives, reports, or becomes aware of a corresponding sensation. However, for at least some neurons, it may be difficult to detect when the threshold level is exceeded because the patient neither displays an outward action nor reports a sensation. This difficulty can arise, for example, when stimulating neurons associated with cognitive or emotional function; or more generally, when stimulating neurons that may be associated with patient functions or responses that are difficult and/or time consuming to readily observe or measure. Such neurons are referred to herein as "silent" neurons. Representative systems and methods for determining a neural stimulation threshold associated with silent neurons are described in detail in U.S. application Ser. No. 11/737,673, entitled "Methods for Establishing Parameters for Neural Stimulation, Including Via Performance of Working Memory Tasks, and Associated Kits," filed on Apr. 19, 2007, which is incorporated herein by reference in its entirety.

Figure 1C:
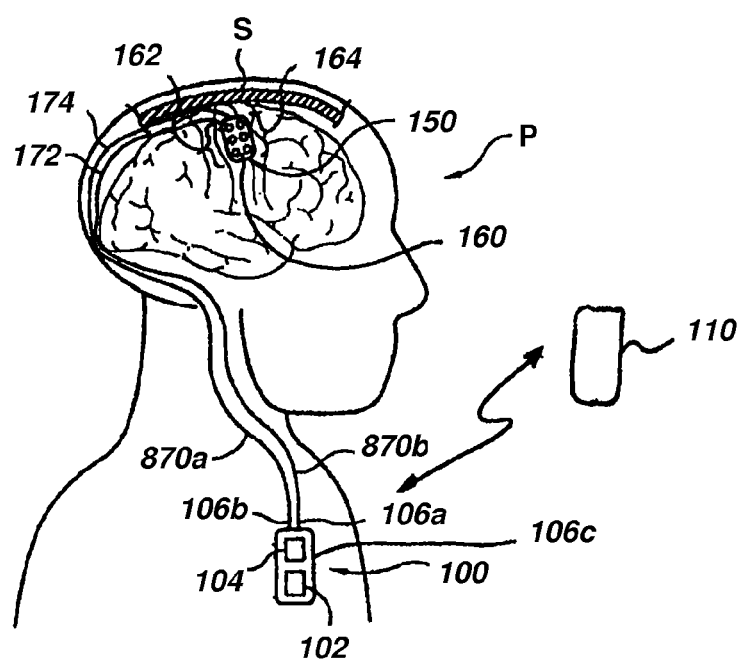
FIG. 1C is a side elevation view of a human brain illustrating prominent brain structures, an electrode array positioned at a representative stimulation site, and an implanted pulse generator at a representative implant site.

FIG. 1C is a side view illustrating a human brain and a system for applying electrical stimulation to a site on a patient. In the illustrated embodiment, a stimulation site is located at or near the surface of the cortex of the patient P. The stimulation system can include a stimulus unit 100 and at least one electrode assembly 150. The electrode assembly 150 shown in FIG. 1C is merely for purposes of illustration and represents only one embodiment of a suitable electrode array; the stimulation system 100 can accordingly include other electrode assemblies in accordance with other embodiments of the invention.

The stimulus unit 100 generates and outputs stimulus signals, such as electrical and/or magnetic stimuli. In the illustrated embodiment, the stimulus unit 100 is generally an implantable pulse generator that is implanted into the patient in a thoracic, abdominal or subclavicular location. In other embodiments, the stimulus unit 100 can be implanted in the skull or just under the scalp S of the patient P. For example, in one specific embodiment, the stimulus unit 100 can be implanted above the neckline or in the skull of the patient as set forth in U.S. Pat. No. 7,010,351, which is incorporated herein by reference in its entirety.

The stimulus unit 100 includes a controller 102 and a pulse system 104. The controller 102 can include a processor, a memory and computer-readable instructions stored on a programmable computer-readable medium. The controller 102 can be implemented as a computer, a microcontroller, or the like. The programmable medium, for example, can include software loaded into the memory and/or hardware that performs, directs and/or facilitates stimulation procedures in accordance embodiments of the invention. In one embodiment, the pulse system 104 can generate signals that are output to a first terminal 106a and/or a second terminal 106b. The first terminal 106a can be biased at a first potential, and the second terminal 106b can be biased at a second potential either equal to or different than the first potential at any given time. In one embodiment, the first potential can have a first polarity and the second potential can have a second polarity or be neutral. For example, the first potential can be either anodal or cathodal, and a second potential can be opposite the first polarity or neutral to facilitate bipolar stimulation. In other embodiments, the first terminal 106a and/or the second terminal 106b can be biased at a given polarity to facilitate unipolar stimulation, in which case a third terminal 106c (which may include a portion of a stimulus unit housing) and/or a remote electrode assembly (not shown) may facilitate electrical current return. The first terminal 106a, the second terminal 106b, and the third terminal 106c can also be operated independently of each other at one or more times in still further embodiments.

The electrode assembly 150 includes a plurality of electrodes including a first set of electrodes 162 and a second set of electrodes 164. The first and second sets of electrodes 162 and 164 are carried by a support member 160, which may be flexible or at least somewhat conformable to a tissue surface. The electrode assembly 150 has at least one first electrode in the first set of electrodes 162 and at least one second electrode in the second set of electrodes 164. The illustrated embodiment has three electrodes in each of the first and second sets of electrodes 162 and 164.

In the illustrated embodiment, the support member 160 is implanted under the skull S of the patient so that the electrodes 162 and 164 contact a stimulation site on, or at least proximate to, the surface of the cortex of the patient. The first set of electrodes 162 is connected to a first lead 172, and the second set of electrodes 164 is connected to a second lead 174. The first lead 172 can electrically couple the first set of electrodes 162 to the first terminal 106a, and the second lead 174 can electrically couple the second set of electrodes 164 to the second terminal 106b. In other embodiments of the stimulation system 100, the leads 172 and 174 can be replaced with wireless transmission components. The pulse system 104 can apply a current to the first set of electrodes 162 independently of applying a current to the second set of electrodes 164. As a result, only the first electrodes 162 can be activated, or only the second electrodes 164 can be activated, or both the first electrodes 162 and the second electrodes 164 can be activated concurrently. In still other embodiments, other subsets of electrodes or individual electrodes can be operated independently of each other such that only a single electrode or any combination of the electrodes can be activated at any given moment. In such embodiments, the pulse system 104 can include additional terminals, such as a fourth terminal and/or a fifth terminal (not shown).

As previously indicated, in various embodiments, the first electrodes 162 and/or the second electrodes 164 can be biased at the same potential in a unipolar or isopolar arrangement. In this embodiment, an electrical signal path may exist between the first electrodes 162 and/or the second electrodes 164 and a separate pole or signal return element that can be implanted in or attached to the exterior of the patient. For example, electrical signal continuity may exist between the electrodes 162, 164 and a portion of the patient's body, a housing of the stimulus unit 100, and/or another point.

C. Embodiments of Methods for Providing Cortical Stimulation

Figure 2A:
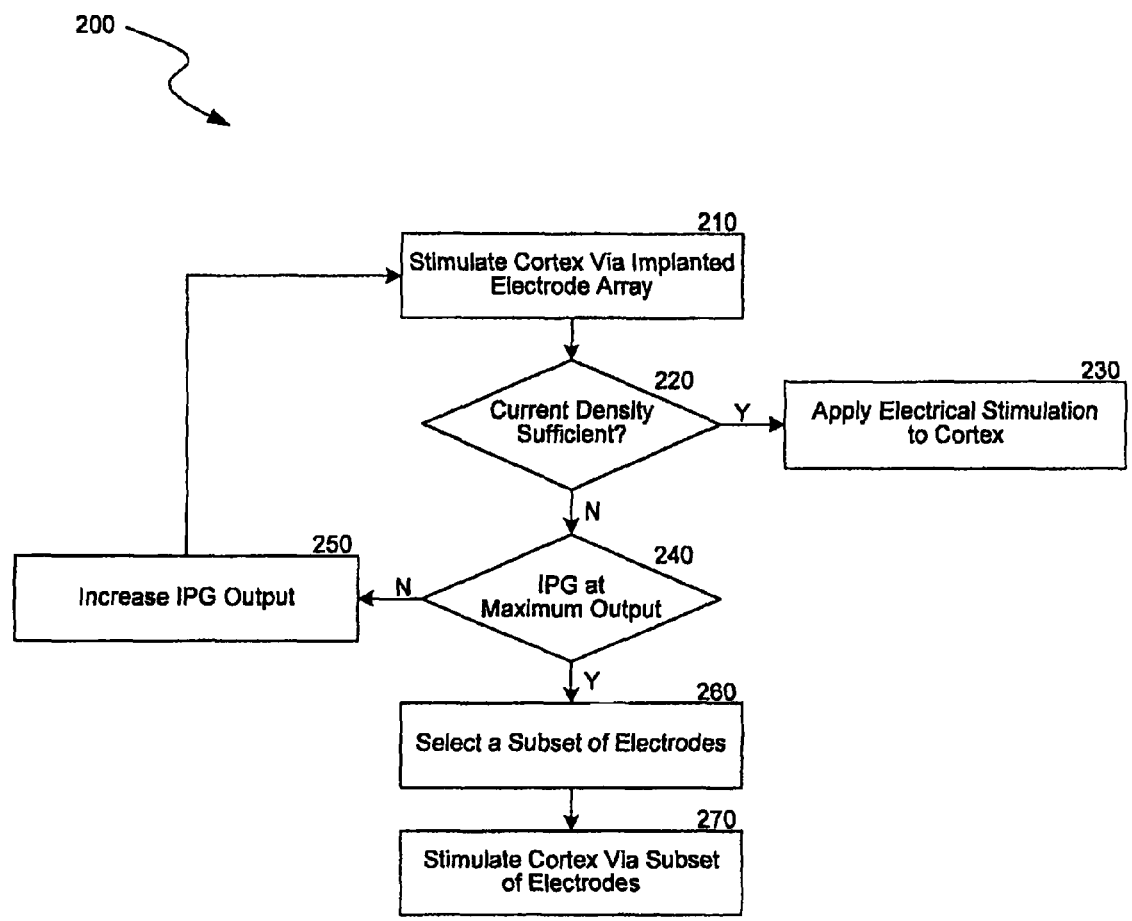
FIG. 2A is a flowchart illustrating a method in accordance with an embodiment of the invention.

FIG. 2A is a flowchart illustrating a method 200 in accordance with an embodiment of the invention. A first stage 210 of the method includes stimulating the cortex via an electrode array implanted at, or at least proximate to, the cortex of the patient. The first stage 210 can be performed by passing an electrical current through an initial or the full plurality of electrodes of the electrode array. Referring to FIG. 1C, for example, one embodiment of the first stage 210 includes passing electrical current concurrently through the first electrodes 162 and the second electrodes 164. A second stage 220 of the method includes determining whether the current density that the active electrodes 162, 164 apply or deliver to the cortex is sufficient to carry out an assessment related to a stimulation therapy (e.g., triggering a movement or other patient response) or facilitate or effectuate the desired stimulation therapy. If the current density is sufficient, the method continues to a third stage 230 in which an electrical stimulation signal is applied to the cortex at a current density appropriate for carrying out the therapy (e.g., approximately 10%-95%, or approximately 25%-75% of a neural activation threshold). However, if the current density at the second stage 220 is not sufficient, the method further includes a fourth stage 240 that involves determining whether the electrical current used to stimulate the cortex in the first stage 210 was at an upper limit or the maximum output of the implanted pulse generator. If the current was not at an upper limit or the maximum output of the pulse generator, the method can continue to an optional fifth stage 250 in which the current from the implanted pulse generator is increased and the first and second stages 210 and 220 are repeated. If the current is at or generally near an upper limit or the maximum output of the pulse generator, the method continues with a sixth stage 260 that involves selecting a subset of the electrodes and a seventh stage 270 that includes stimulating the cortex via the subset of electrodes. The stimulation provided via the subset of electrodes produces a higher current density in the cortical area at or beneath the subset of electrodes compared to passing the current through the initial or full plurality of electrodes in the first stage 210.

The method 200 can be particularly useful for determining a threshold, suprathreshold, or activation current level for therapies that include the application of subthreshold stimulation to the cortex. As explained above, an activation threshold for a stimulation site can be determined by applying the stimulation at increasing levels until the stimulation causes an involuntary movement, sensation and/or other type of measurable, monitorable, calculable, or estimable response in the patient. However, when the electrical current is applied or delivered using more than a certain number of electrodes, an involuntary response may not be manifested in a patient even at the maximum output of the implanted pulse generator. The current density in the cortex in such circumstances is not sufficient to evoke or induce the activation response, but it is impractical to replace an implanted pulse generator with another one having a higher output level. In such instances, the electrical current may be applied to the cortex using fewer electrodes to increase the current density in those portion(s) of the cortex stimulated by the active electrodes. In various situations, an activation response can be induced in neurons within a target neural population through the application or delivery of a higher current density when the electrical current passes through a smaller number of electrodes, even though less surface area of the cortex is subject to stimulation. As a result, one embodiment of the method 200 is particularly useful for determining an activation threshold corresponding to a stimulation site in a specific patient, which can then be used to establish, calculate, or estimate a subthreshold stimulation level or signal intensity for carrying out a cortical stimulation therapy.

Figure 2B:
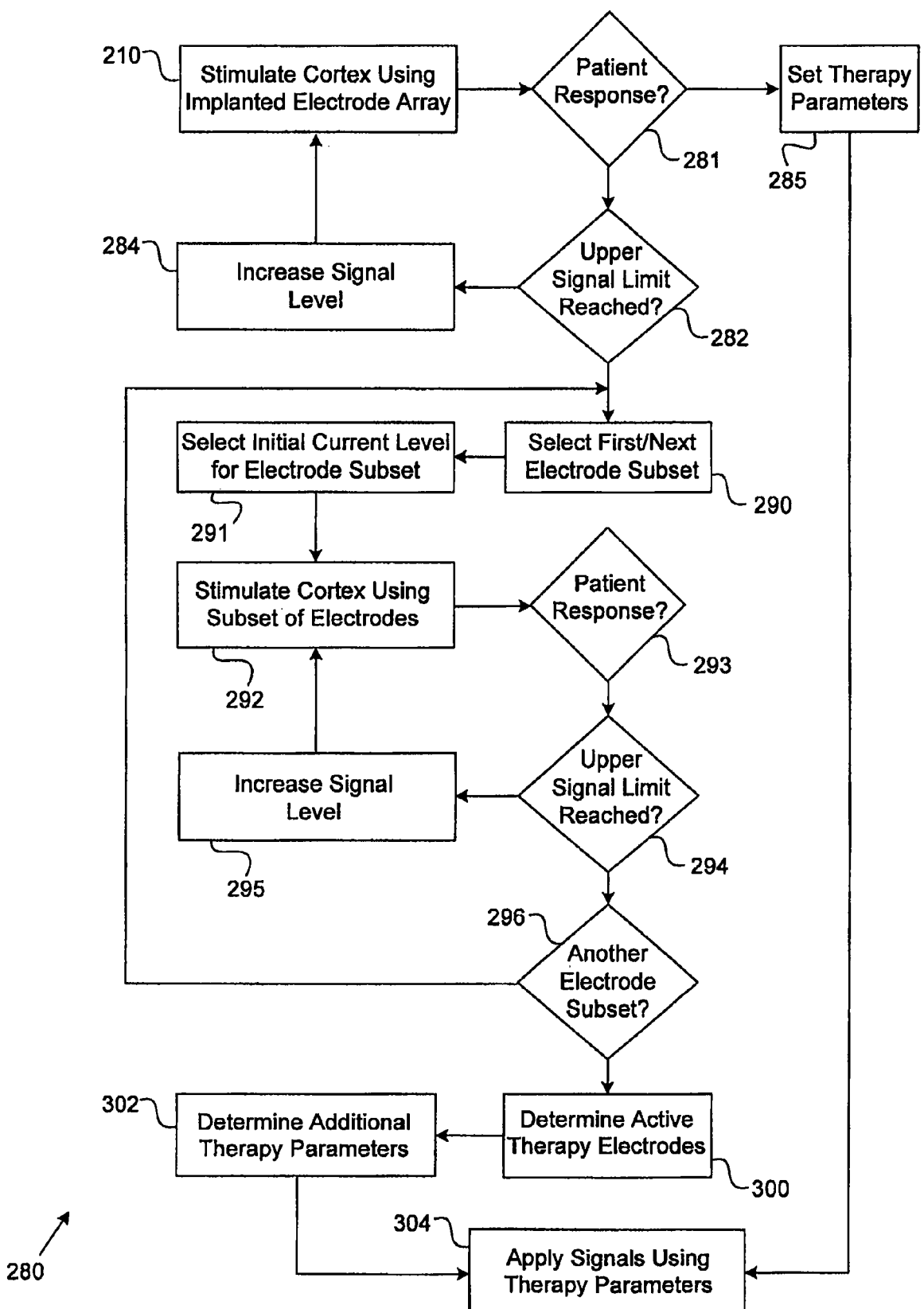
FIG. 2B is a flowchart illustrating a method in accordance with another embodiment of the invention.

FIG. 2B is a flowchart illustrating a method 280 in accordance with another embodiment of the invention for determining an activation threshold at a specific stimulation site. The method 280 includes the first stage 210 of stimulating the cortex via an implanted electrode array and a second stage 281 of determining whether the stimulation induced a response or effect in the patient. The second stage 281, for example, can include determining whether the stimulation induced a motor, sensory, cognitive, emotional, and/or other type of measurable, monitorable, detectable, or reportable response or effect in the patient.

As explained above, the stimulation of the first stage 210 may not induce an intended response in the patient. If this occurs, the method 280 continues with a third stage 282 of determining whether the current level is at an upper limit, or the maximum output of the implanted pulse generator has been reached. If an upper current limit or the maximum output of the pulse generator has not been reached, the method can continue with a fourth stage 284 of increasing the output of the implanted pulse generator (e.g., by an increment of 0.5 or 1.0 mA), and this aspect of the method can further include repeating the first stage 210 and at least the second stage 281.

If the stimulation from the first stage 210 induces a response in the patient, the method continues with a fifth stage 285 of selecting at least one set of stimulation parameters for application during a therapy period. In general, the set of stimulation parameters can be selected based upon a lowest or near-lowest current level that induced a patient response. In various embodiments, the fifth stage 285 may involve defining or setting at least one subthreshold current level that equals or correlates to approximately 10%-95%, or approximately 25%-75% (e.g., approximately 50%), of a current level that induced a patient response. The method further includes a fifteenth stage 304 that includes stimulating the cortex at one or more selected subthreshold and/or suprathreshold levels at one or more times.

If the current level of the implanted pulse generator is at the maximum output in the third stage 282, the method 280 continues with a sixth stage 290 of selecting a subset of the plurality of electrodes of the electrode array. For example, if a total of 6 electrodes were used to stimulate the cortex in the first stage 210, then a smaller number of electrodes, for example, 3 electrodes, can be selected for stimulating the cortex in the sixth stage 290. The particular subset of electrodes selected may be based upon current density considerations, electrode array design, pulse generator design, neural imaging results, EEG or ECoG measurements, patient symptomology, and/or functional or anatomical considerations. For example, in an embodiment employing an electrode array having 2 rows of 3 electrodes, the first stage 210 may involve stimulation with both rows of electrodes, while the sixth stage 290 may involve selecting one particular row of electrodes. As another example, in an embodiment employing an electrode array having 3 rows of 4 electrodes, the sixth stage 290 may involve selecting a subset of electrodes (e.g., a single 4 electrode row) positioned closest to or furthest from a particular neuroanatomical structure or feature (e.g., the central sulcus, or a particular boundary or region corresponding to the motor cortex, the premotor cortex, the supplementary motor area (SMA), the primary or secondary somatosensory cortex, the primary or secondary auditory cortex, the prefrontal cortex (e.g., the dorsolateral prefrontal cortex (DLPFC)), and/or another area).

The method 280 continues with a seventh stage 291 that includes selecting an initial current level to be delivered using the electrode subset presently under consideration. With respect to various embodiments, in the seventh stage 291 the current output level of the pulse generator is initially scaled or adjusted to a level that is lower than the current level most-recently applied in association with the first stage 210. An adjusted current level may be based upon the number of electrodes within the subset of electrodes presently under consideration in view of a) the number of electrodes associated with the first stage 210; b) the number of electrodes associated with a previously considered subset of electrodes; c) anatomical placement differences between distinct electrode subsets; and/or c) electrode design considerations.

In certain embodiments, if the first stage 210 utilized k active electrodes up to a current level of $(l_{k\,Max})$ mA, then the seventh stage 291 may utilize (k−n) electrodes beginning with a current level scaled by approximately $l_{k\,Max}*((k-n)/k)$. Such current level scaling may establish a correlation or approximate match between stimulation conditions involving different numbers of electrodes. For instance, if the first stage 210 utilized 6 active electrodes and a maximum applied current level (e.g., at approximately the maximum pulse generator output) of 13.0 mA, in particular embodiments the seventh stage 291 may utilize 3 active electrodes that initially deliver stimulation at a current level of approximately 6.5 mA to provide or approximately provide an initial current density continuity across different electrode configurations. In some embodiments, the current level initially applied in the seventh stage 291 may further be adjusted by a current offset value, for instance, approximately −0.5 or −1.0 mA, or approximately +0.5 or +1.0 mA. Additionally or alternatively, the current level applied in the seventh stage 291 may also be adjusted in accordance with an impedance factor $z_a$. For instance, the seventh stage 291 may initially apply a current level scaled by $z_a*((k-n)/k)$. The impedance adjustment factor may be based upon an impedance relationship between k active electrodes and (k−n) active electrodes in view of a) anatomical electrode position differences; and/or b) possible impedance scaling non-uniformity. In other embodiments the current level of the pulse generator in the seventh stage 291 can be at, or below but near, the maximum output level of the pulse generator.

The method 280 continues with an eighth stage 292 that includes stimulating the cortex using the presently selected subset of electrodes, and a ninth stage 293 of determining whether the stimulation through this subset of the electrodes induced a response or effect in the patient. The type of response in the ninth stage 293 can be the same as, or possibly different from, the type of response in the second stage 281. If there is no response in the patient, the method continues with a tenth stage 294 of determining whether the current density or the current level is at an upper limit (e.g., a maximum allowable current density, or the maximum output of the implanted pulse generator). If an upper signal limit has not been reached, the method can continue with an eleventh stage 295 that involves increasing the current level (e.g., by an increment of 0.25, 0.5, or 1.0 mA). The amount by which the current level is increased may be the same as or different from that associated with the fourth stage 284 (e.g., a smaller increment in accordance with a difference in a number of electrically active electrodes). This electrical current increment aspect of the method 280 can further include repeating at least some of the eighth through the eleventh stages 292-295, possibly until a patient response is detected and a minimum or near-minimum current level at which a response occurred is stored or otherwise noted.

In some embodiments, if the tenth stage 294 determines that a maximum current density or current level has been reached, the method 280 continues with a twelfth stage 296 that determines whether to consider a subsequent subset of electrodes. If so, the method 280 may return to or repeat the sixth stage 290 to select a different subset of electrodes for consideration. For instance, if the first stage 210 involved stimulation using 6 electrodes, and the seventh through eleventh stages most recently involved stimulation using a first electrode subset having 3 electrodes, the twelfth stage 296 may involve stimulation using a distinct second electrode subset having 3 electrodes, or a second electrode subset having 2 electrodes. In particular embodiments, this aspect of the method 280 can involve repeating at least some of the sixth through the twelfth stages 290-296, for example, to determine whether at least one threshold current level exists in view of multiple electrode subsets; or to establish or estimate a threshold current level—electrode subset correlation (which may be electronically stored or otherwise noted).

Following the selection of any given electrode subset, an initial current level at which to stimulate the patient may be selected in the seventh stage 291 based upon a previously applied current level or current density; the number of electrodes in a previously considered electrode subset; the number of electrodes within the newly selected electrode subset; anatomical position differences between active electrodes in a previously considered electrode subset and the newly considered electrode subset; and/or other factors. For instance, if a first electrode subset included 3 electrodes and a second electrode subset includes 2 electrodes, an initial current level at which to test for a neural activation threshold using 2 electrodes may be scaled by approximately (⅔) relative to an initial current level applied to the patient using 3 electrodes.

If the ninth stage 293 determines that a stimulation response is induced or evoked in the patient, or the twelfth stage 296 determines that a sufficient number of electrode subsets have been considered, the method 280 can further include a thirteenth stage 300 that involves determining a subset of electrodes to which a signal is to be applied during a therapy period or session; and a fourteenth stage 302 that involves selecting or determining particular stimulation parameters. Such stimulation parameters can include one or more therapy current levels, voltages, pulse widths, inter-pulse repetition frequencies, intra-pulse burst patterns, signal modulation functions, and/or other parameters (e.g., a duty cycle, or a therapy period duration). The method 280 further includes a fifteenth stage 304 that involves the application of stimulation signals to the patient in accordance with an active electrode subset and a set of stimulation parameters determined in association with the thirteenth and fourteenth stages 302, 304, respectively.

In general, if a stimulation response was induced in the patient using r electrodes at an applied current of $1_r$ mA, then a threshold current density may be approximately defined as $J_r=(1_r/r)$ mA per active electrode. Subthreshold stimulation using s electrodes to provide p % of the threshold current density $J_r$ can correspondingly involve a current level of $1_s=p \%*(s*J_r)$ mA. As a representative example to aid understanding, in the event that a patient response (e.g., an evoked potential) occurred at a current level of 8 mA using 3 electrodes, then a corresponding threshold current density equals 2.67 mA/electrode. A therapy session may involve the application of subthreshold stimulation at 50% of this threshold current density by using 6 electrodes to apply 8 mA of current to the patient. Similarly, based upon a threshold current level of 8 mA using 3 electrodes, subthreshold stimulation at 25% or 75% of the threshold current density may involve the respective application of 4 mA or 12 mA to a stimulation site using 6 electrodes.

As another representative example, if a patient response occurs in association with the application of approximately 6 mA of current to a stimulation site using 3 electrodes, then a corresponding threshold current density equals approximately 2 mA/electrode. A therapy session involving the application of subthreshold stimulation at 50% of this threshold current density (i.e., subthreshold stimulation applied at 1 mA/electrode) may apply 6 mA using 6 electrodes; 4 mA using a first set of 4 electrodes; 4 mA using a second set of 4 electrodes; 2 mA using 2 electrodes; or some combination of mathematically equivalent current density configurations that differ in terms of the number of electrically active electrodes, spatial distribution of electrically active electrodes, and/or overall current level applied.

Referring again to FIG. 2B, in certain instances an intended type of patient response may not be detected or measured by the ninth stage 293 for the electrode subsets considered in the context of the sixth through the twelfth stages 290-296. In such situations, the thirteenth stage 300 may assign or define a default set of stimulation parameters that includes a default current level (e.g., 6.5 mA) and/or a default electrode configuration (e.g., 100%, 80%, or 50% of available electrodes active during a therapy session). Alternatively, the thirteenth stage 300 may prompt a medical professional to input one or more current levels, electrode configurations or other stimulation parameters for a therapy session (e.g., via an external programming device 110).

The method 280 illustrated in FIG. 2B enables determining an activation threshold associated with a stimulation site for a patient even if the output of the implanted pulse generator is not sufficient to induce a response in the patient using all, or at least a large or substantial number of, the electrodes in an electrode array. The method 280 accordingly allows practitioners to compensate for functional and/or anatomical differences in patients, and may increase a likelihood of determining an activation threshold and applying a therapeutically relevant signal intensity in view of pulse generator power limitations. In certain situations, this feature may be useful when the stimulation occurs over a long period of time (e.g., days, weeks, months, or years) because an activation threshold of a specific stimulation site or region may change. The method 280 may reduce a likelihood of delivering therapy in accordance with suboptimal or less desirable parameter settings, or explanting an implanted pulse generator (e.g., following a neural consolidation period or other intermediate therapy stage during which electrical stimulation may be reduced or interrupted) due to pulse generator power limitations.

Figure 3A:
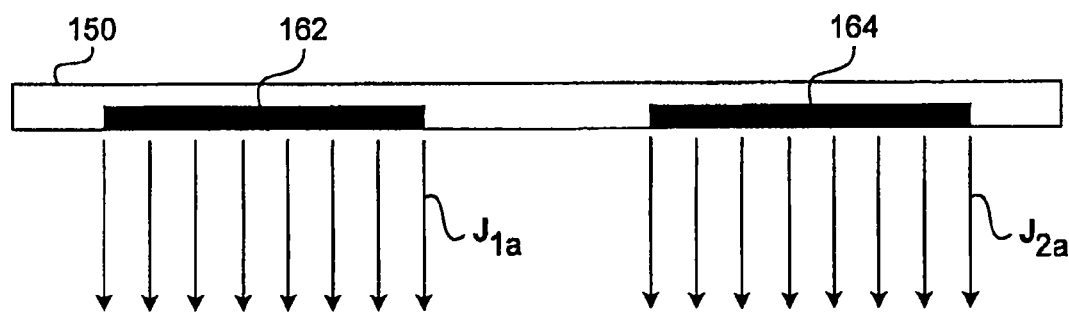
FIGS. 3A-3C are cross-sectional views of the operation of an implanted electrode array in accordance with embodiments of the invention.
Figure 3B:
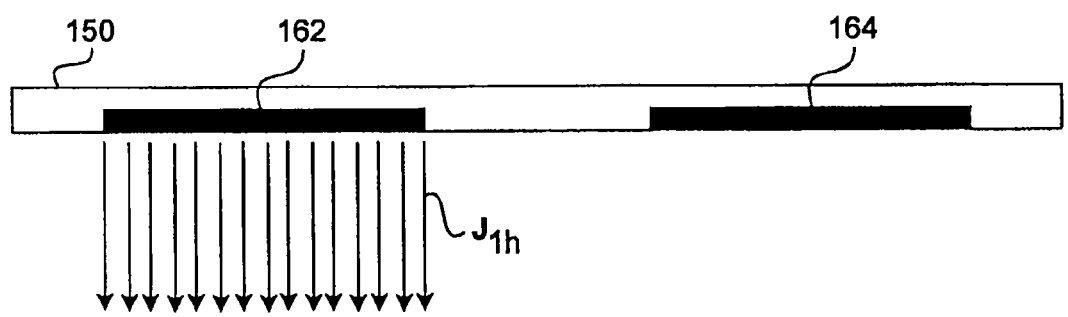
Figure 3C:
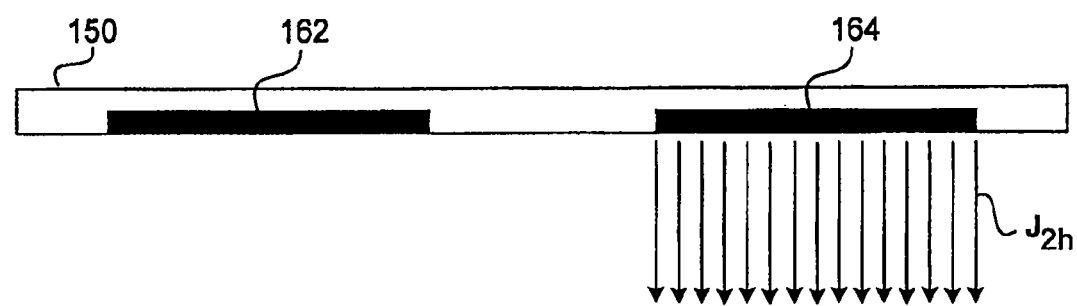

FIGS. 3A-3C schematically illustrate particular aspects of methods in accordance with the present invention, such as methods 200 or 280 described above with reference to FIGS. 2A and 2B. For ease of understanding, FIGS. 3A-3C are directed toward the application of signals using a constant-current stimulation device, such that impedance variations between different electrode configurations can generally be ignored (in view of actual stimulation device limitations, as will be understood by those of ordinary skill in the art). Additionally, FIGS. 3A-3C are directed toward a unipolar signal configuration, in which at least one remote conductive element (not shown) provides a current return path. Furthermore, for simplicity, FIGS. 3A-3C are directed toward an electrode assembly 150 having generally uniform electrodes of essentially equal surface area and/or periphery.

FIG. 3A, more specifically, graphically illustrates stimulating the cortex via the plurality of electrodes 162 and 164 of the electrode array 150 implanted at or near the cortex of the patient. The application of an electrical current to the first and second electrodes 162 and 164 results in the establishment of a first current density $J_{1a}$ and a second current density $J_{2a}$ corresponding to the first electrode(s) 162 and the second electrode(s) 164, respectively. In this embodiment, the first and second current densities are approximately equal to each other, and are each illustrated as a set of vertical lines of equal line spacing or density. Those of ordinary skill in the art will understand that the current delivered by any given electrode generally exhibits a peak at or proximate to the electrode's periphery, and thus spatial variation(s) in current density may be more complex than depicted in FIG. 3A.

When the current supplied by the stimulation device is at an upper limit or maximum level (e.g., a maximum output of an implanted pulse generator relative to a given signal application duration), the first current density $J_{1a}$ and the second current density $J_{1a}$ may be insufficient to induce a desired response in the patient and/or carry out a particular stimulation therapy.

FIG. 3B graphically illustrates stimulating the cortex via a subset of the electrodes, for instance, at a subsequent stage of method 200 and/or 280 described above. In this particular example, the current is applied to at least one of the first electrodes 162 to establish a first higher current density $J_{1h}$ that exceeds either of the first current density $J_{1a}$ or the second current density $J_{2a}$ of FIG. 3A. The first higher current density $J_{1h}$ can provide an elevated peak or average current level in the region(s) of the cortex adjacent to the first electrodes 162 even if the current level or amplitude output by the stimulation device is less than the output level when the current passed concurrently through the first electrodes 162 and the second electrodes 164 at the first stage 210 of method 200 and/or 280.

FIG. 3C illustrates an alternative embodiment in which the stimulation is applied via at least one of the second electrodes 164 to create a subsequent second higher current density $J_{2h}$. The second higher current density $J_{2h}$ can be applied to a different area of the cortex than the first higher current density $J_{1h}$ provide a higher current density to a distinct cortical region. The stimulation can be applied to the second electrodes 164 independently of the first electrodes 162, in lieu of or in addition to applying stimulation via the first electrodes 162.

Referring to FIGS. 3B and 3C in comparison to FIG. 3A, the first and second higher current densities $J_{1h}$ and $J_{2h}$ can be greater than either of the first or second current densities $J_{1a}$ and $J_{2a}$ associated with FIG. 3A. Such an increased current density may facilitate or trigger the activation of enough neurons in the cortex to cause an effect or response in the patient that did not occur with the first and second current densities $J_{1a}$ and $J_{2a}$. As explained above, this can be particularly useful for determining an activation threshold in a specific patient when the maximum output of the pulse generator is not sufficient to induce a response in the patient when the current is applied across a larger number of electrodes of the electrode array. Moreover, a higher current density $J_{1h}$ or $J_{2h}$ is expected to affect deeper cortical tissue compared to the first or second current density $J_{1a}$ and $J_{2a}$. This may enable additional and/or different neurons to be triggered to determine the activation threshold of a specific patient. The additional current density and/or a greater penetration of a corresponding electric field resulting from delivering current with fewer electrodes may also enable additional therapies to be carried out and/or enhance the efficacy of therapies compared to applying a given current level or the maximum output of the pulse generator across more electrodes.

Figure 4A:
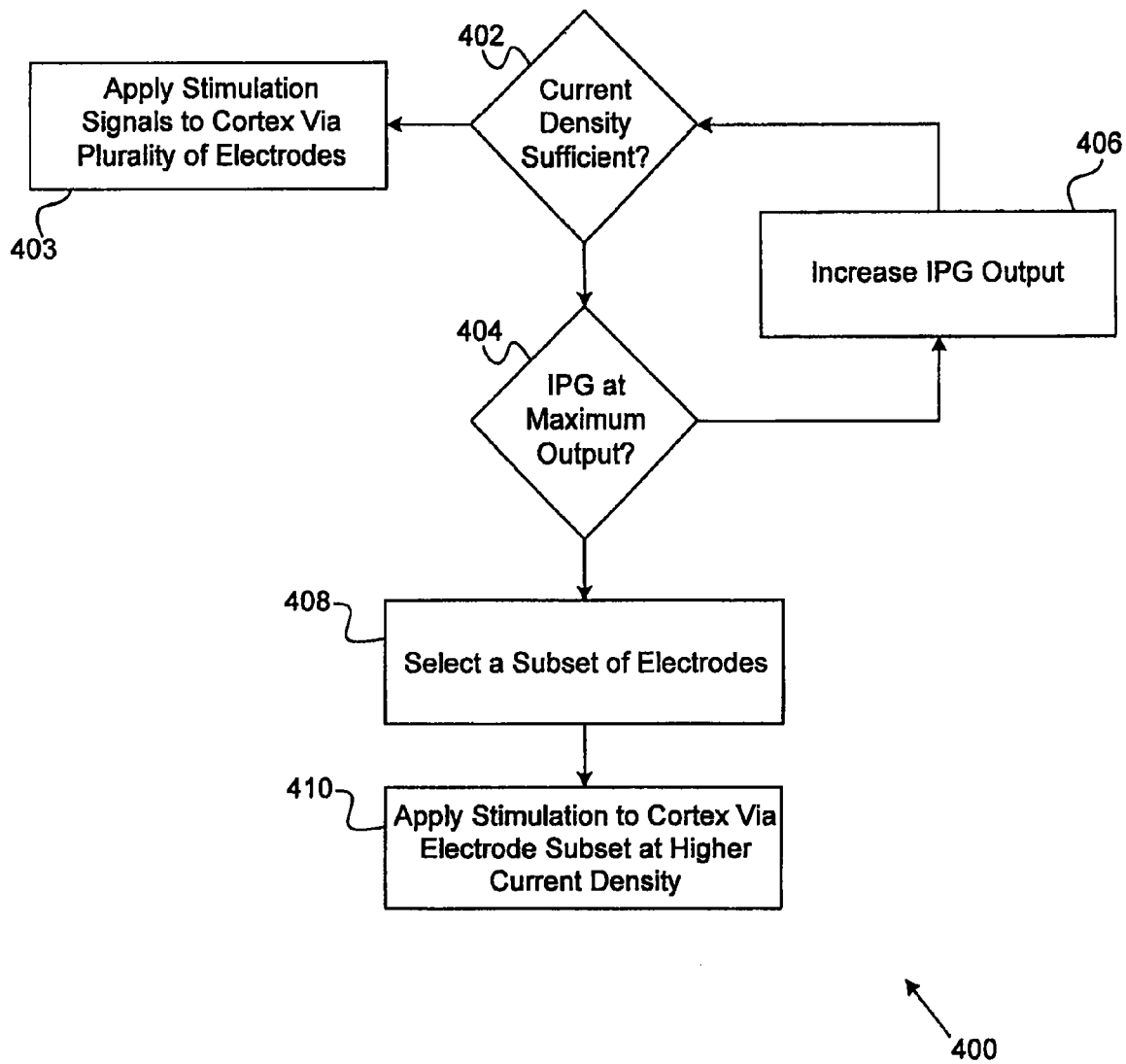
FIG. 4A is a flowchart of a method in accordance with another embodiment of the invention.

FIG. 4A is a flowchart illustrating a method 400 in accordance with another embodiment of the invention. In this embodiment, the method includes a first stage 402 of determining whether the applied current or the associated current density is sufficient to carry out a specific therapy and/or assess a parameter for use in a therapy. If the current is sufficient, the method continues with a second stage 403 of applying the current to the cortex via a plurality of electrodes positioned at, or at least proximate to, the cortex. If the current density at the first stage 402 is insufficient, the method continues with a third stage 404 that involves determining whether the current is at the maximum output level of the implanted pulse generator. If the implanted pulse generator is not outputting at its maximum level, the method can optionally continue with a fourth stage 406 that includes increasing the output of the implanted pulse generator and then repeating the first stage 402. However, if the output of the implanted pulse generator is at the maximum, the method continues with a fifth stage 408 of selecting a subset of the plurality of electrodes and a sixth stage 410 of applying the stimulation to the cortex via the subset of the plurality of the electrodes. The current applied to the subset of the plurality of electrodes causes a higher current density at the regions of the cortex adjacent the subset of electrodes as explained above. The current applied to the subset of the electrodes may be at the maximum output of the implanted pulse generator, but in other embodiments the output of the pulse generator may be less than its maximum output. Even when the output of the implanted pulse generator is less than its maximum, the foregoing methods may still provide a higher current density in the cortex so long as the current output from the pulse generator is still proportionally higher than the ratio of the surface area of the subset of the electrodes to the surface area of the whole or original plurality of electrodes.

The method 400 illustrated in FIG. 4A can be useful to carry out a cortical stimulation therapy that would benefit from a higher current density than a pulse generator can provide when the current is simultaneously applied or delivered to a large number of electrodes of the electrode array. As further detailed below, the current can be multiplexed across two or more different subsets of electrodes in which each subset has at least one electrode. The method 400 can be used to apply the stimulation therapy to deeper portions of the cortex and/or across larger areas of the cortex depending upon the particular therapy. Referring back to FIG. 1C, for example, it may be desirable to apply the stimulation therapy across the entire 2×3 electrode array to stimulate portions of both the motor cortex and the sensory cortex as opposed to stimulating regions within just one of the motor cortex or the sensory cortex across a single 1×3 array. Such a broad area application, however, may distribute the current across a larger surface area such that the output of the implanted pulse generator is not sufficient to carry out a desired therapy, possibly limiting or reducing therapeutic efficacy. When this occurs, the method 400 illustrated in FIG. 4A can be implemented to increase the current density in the cortex at each sub-area to provide a desired therapy across a larger total area.

Figure 4B:
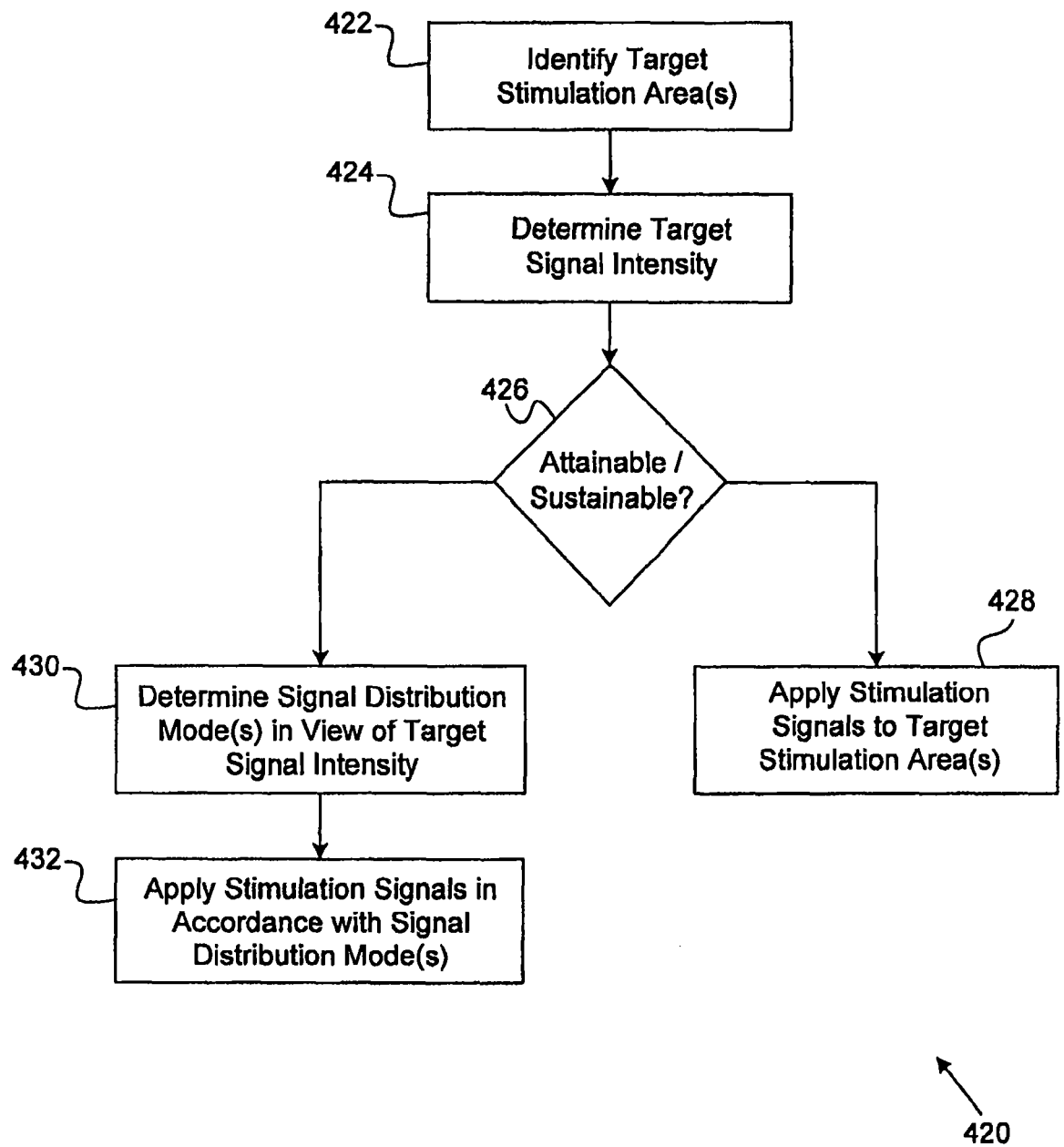
FIG. 4B is a flowchart illustrating a method in accordance with still another embodiment of the invention.

FIG. 4B is a flowchart illustrating a method 420 in accordance with another embodiment of the invention. In this embodiment, the method 420 includes a first stage 422 of identifying a set of target stimulation areas to which neural stimulation is to be applied using a plurality of electrodes. The set of target stimulation areas may include or span portions of a single neurofunctional region, or multiple neurofunctional regions. For example, a set of target stimulation areas may include portions of the motor cortex, the premotor cortex, the SMA, the prefrontal cortex, the orbitofrontal cortex (OFC), the primary auditory cortex, the secondary auditory cortex, or the visual cortex. Alternatively, a set of target stimulation areas may include portions of the motor and premotor, somatosensory, and/or supplementary motor cortices; the motor or premotor cortex and a language-related area (e.g., Broca's area and/or Wernicke's area); the primary and secondary auditory cortices; the secondary auditory cortex and the secondary somatosensory cortex; the right and left dorsolateral prefrontal cortices; the dorsolateral prefrontal cortex and the ventrolateral and/or ventromedial prefrontal cortex; or portions of other neural regions.

The method 420 further includes a second stage 424 of determining or estimating a target or maximum signal intensity (e.g., a current level) intended for delivery across a maximum or largest number of simultaneously active electrodes. The method 420 also includes a third stage 426 of determining whether the target signal intensity is attainable or sustainable in view of stimulation device limitations or particular signal application constraints. If so, the method 420 includes a fourth stage 428 of applying stimulation signals to the target stimulation areas.

In the event that the target signal intensity is not attainable or sustainable, the method includes a fifth stage 430 of determining at least one signal distribution mode. In various embodiments, a signal distribution mode can specify or define a manner of spatial and/or temporal signal partitioning. For example, a signal distribution mode may define a smaller number of simultaneously active electrodes at any given time. The application of stimulation signals in accordance with a signal distribution mode can facilitate, induce, or result in a physiologic response or therapeutic effect that may be generally equivalent or analogous to, or possibly more effective than, that which would be expected in response to the simultaneous application of the target signal intensity across a larger number of electrodes. Finally, the method 420 also includes a sixth stage 432 of applying stimulation signals to the patient in accordance at least one signal distribution mode.

In various embodiments described herein, program instructions stored upon a computer readable medium (e.g., within an external programming device 110) may facilitate the automatic or semi-automatic definition or determination of one or more acceptable or allowable signal distribution modes. Such program instructions may retrieve or request electrode assembly design information (e.g., a total number of electrodes, and available electrode coupling pathways) to facilitate the selection, definition, or identification of an appropriate signal distribution mode. One or more signal distribution modes can be predetermined or prestored on a computer readable medium (e.g., within the implantable pulse generator and/or an external programming device 110). A particular signal distribution mode can be selected, determined, or adjusted by a practitioner on a patient-specific basis based upon therapeutic efficacy. Representative types of signal distribution modes involving signal multiplexing are described hereafter with respect to FIGS. 5 and 6.

Figure 5:
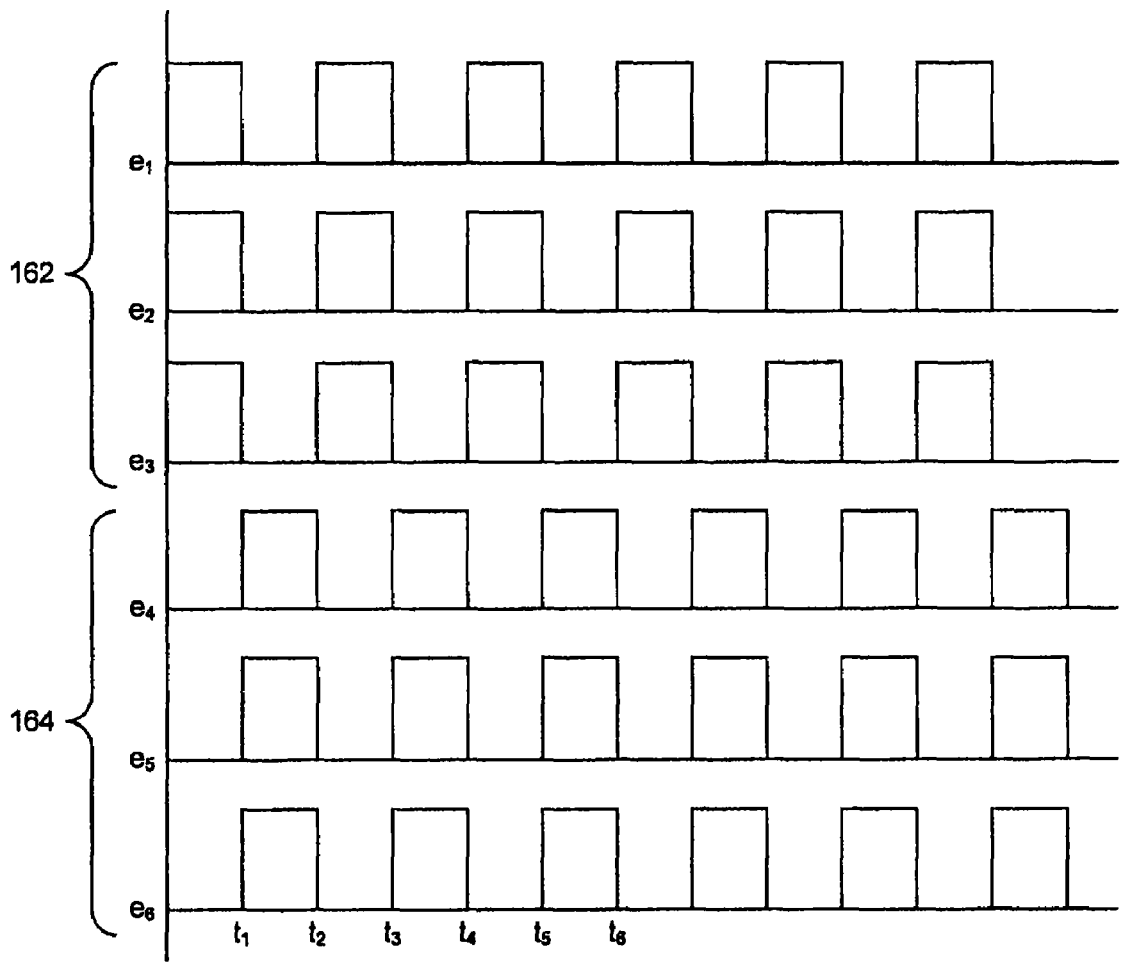
FIG. 5 is a graph illustrating a multiplexing mode based on a split duty cycle between the electrodes in accordance with an embodiment of the invention.

FIG. 5 is a timing diagram illustrating an embodiment of a method 400, 420 in accordance with the present invention being carried out across the first electrodes 162 and the second electrodes 164 of the electrode array 150 illustrated in FIG. 1C. As indicated in this timing diagram, the pulse generator multiplexes its signal output across electrodes $e_1$-$e_3$ of the subset of first electrodes 162 and electrodes $e_4$-$e_6$ of the subset of second electrodes 164. More specifically, the current is applied to the subset of the first electrodes 162 for a first on-period 0-$t_1$, and then the current is applied to the subset of second electrodes 164 for a second on-period of time $t_1$-$t_2$. As shown in FIG. 5, the alternating activation of the first subset of electrodes 162 and the second subset of electrodes 164 can continue or repeat across subsequent on-periods in an identical or analogous manner. During each on-period, the current can be applied at a desired pulse repetition frequency. In many applications, the frequency is from approximately 1.0 Hz-1000 Hz, or more specifically between 10 Hz-250 Hz, or still more specifically about 40 Hz-150 Hz (e.g., approximately 50 Hz-100 Hz). The amplitude of the current is adjusted using the output of the implanted pulse generator to provide a desired level of subthreshold or suprathreshold stimulation.

Figure 6:
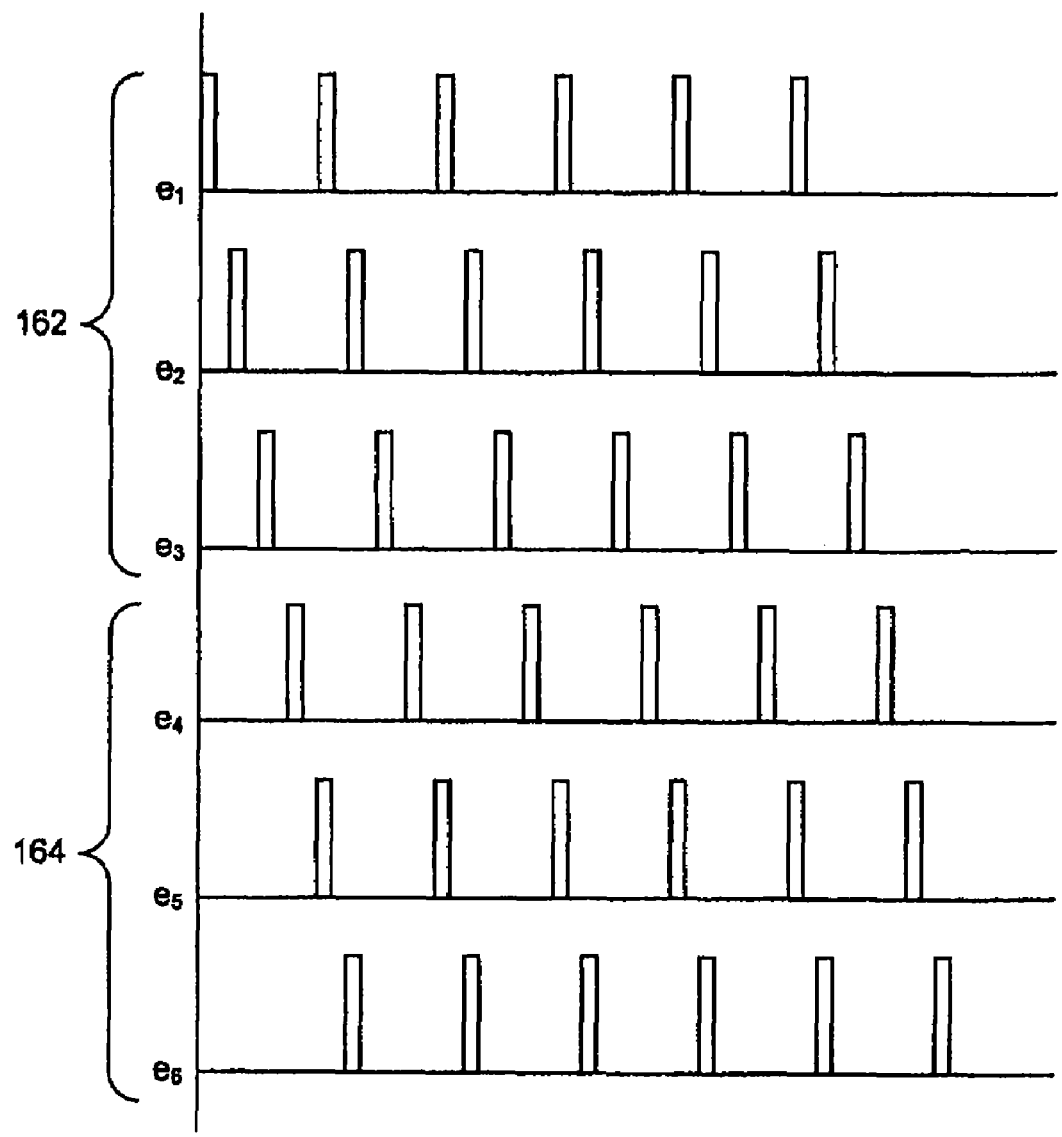
FIG. 6 is a graph illustrating another multiplexing mode across electrodes in accordance with an embodiment of the invention.

FIG. 6 is a timing diagram illustrating another form of multiplexing across the subset of first electrodes 162 and the subset of second electrodes 164. More specifically, the pulse generator can provide a signal having a frequency equal to the product of a target frequency that is to be applied to the cortex for the therapy times and at least the number of simultaneously active individual electrodes or separate subsets of electrodes. For example, if the desired frequency to be applied to the cortex is 50 Hz and the electrode array has six independent electrodes, the pulse generator can output a signal at 300 Hz that is multiplexed at each cycle serially across individual electrodes $e_1$-$e_6$ such that the effective signal applied to each electrode is 50 Hz. In other embodiments, each subset of electrodes can have a plurality of commonly activated electrodes. For example, if electrodes $e_1$-$e_3$ are activated simultaneously and electrodes $e_4$-$e_6$ are activated simultaneously, then the pulse generator can output a signal at 100 Hz that is frequency multiplexed to provide a 50 Hz signal to each electrode subset (effectively providing stimulation at 100 Hz). Depending upon embodiment details, electrode subsets may be activated in predetermined or aperiodic manners or sequences.

Various embodiments involving signal multiplexing techniques such as those described in relation to FIGS. 5 and 6 can be applied to any of the methods (e.g., methods 200, 280, 400, and/or 420) described herein. Such methods can accordingly be used to apply cortical stimulation across a larger or wider area of the cortex without having to explant a pulse generator and replace it with another one having a higher output level. Additionally, multiplexing the output of the pulse generator across the electrode array during a given time period to increase the current density may reduce the energy consumed by the pulse generator compared to providing an output sufficient to generate the same current density continuously across all of the electrodes of the electrode array during an identical time period. This feature is particularly useful for implanted pulse generators because prolonging battery life can be useful in view of long-term therapies. Therefore, various methods in accordance with the present invention are expected to provide more flexibility in applying neural stimulation to treat patients.

In particular situations, a treatment program or therapy regimen may involve the application of stimulation signals to one or more cortical or other neural targets, populations, sites, areas, or regions, possibly in a selective manner based upon a plurality of measured and/or estimated neural activation thresholds corresponding to such neural targets or patient symptomology. When a treatment program involves the application of stimulation signals to multiple neural regions, the regions to which stimulation signals are directed can correspond to one or more types of neural function. In particular embodiments, the application of stimulation signals to multiple stimulation sites may involve cortical stimulation alone; or cortical stimulation in association or conjunction with subcortical or deep brain stimulation (DBS), spinal column stimulation (SCS), cerebellar stimulation, and/or peripheral nerve stimulation (PNS). Typically, any given type of neural stimulation will involve a corresponding appropriate type of electrode assembly (e.g., an electrode array such as that described above; a DBS electrode; or a nerve cuff electrode) in a manner understood by those of ordinary skill in the art. Representative types of systems for applying cortical stimulation in combination or association with other types of stimulation are described in U.S. patent application Ser. No. 11/344,453, filed Jan. 30, 2006 and incorporated herein by reference in its entirety.

The stimulation of multiple neural regions may facilitate or effectuate the treatment of multi-symptom neurologic dysfunction. Additionally or alternatively, the stimulation of multiple neural populations can enhance therapeutic efficacy when addressing a single or multiple types of neurologic dysfunction. For instance, the application of stimulation signals to a first neural population can synergistically affect an extent to which a second neural population responds to stimulation signals. The stimulation of multiple neural populations can also facilitate the evaluation of patient symptom extent or severity, or the assessment of patient functional gains over time.

Figure 4C:
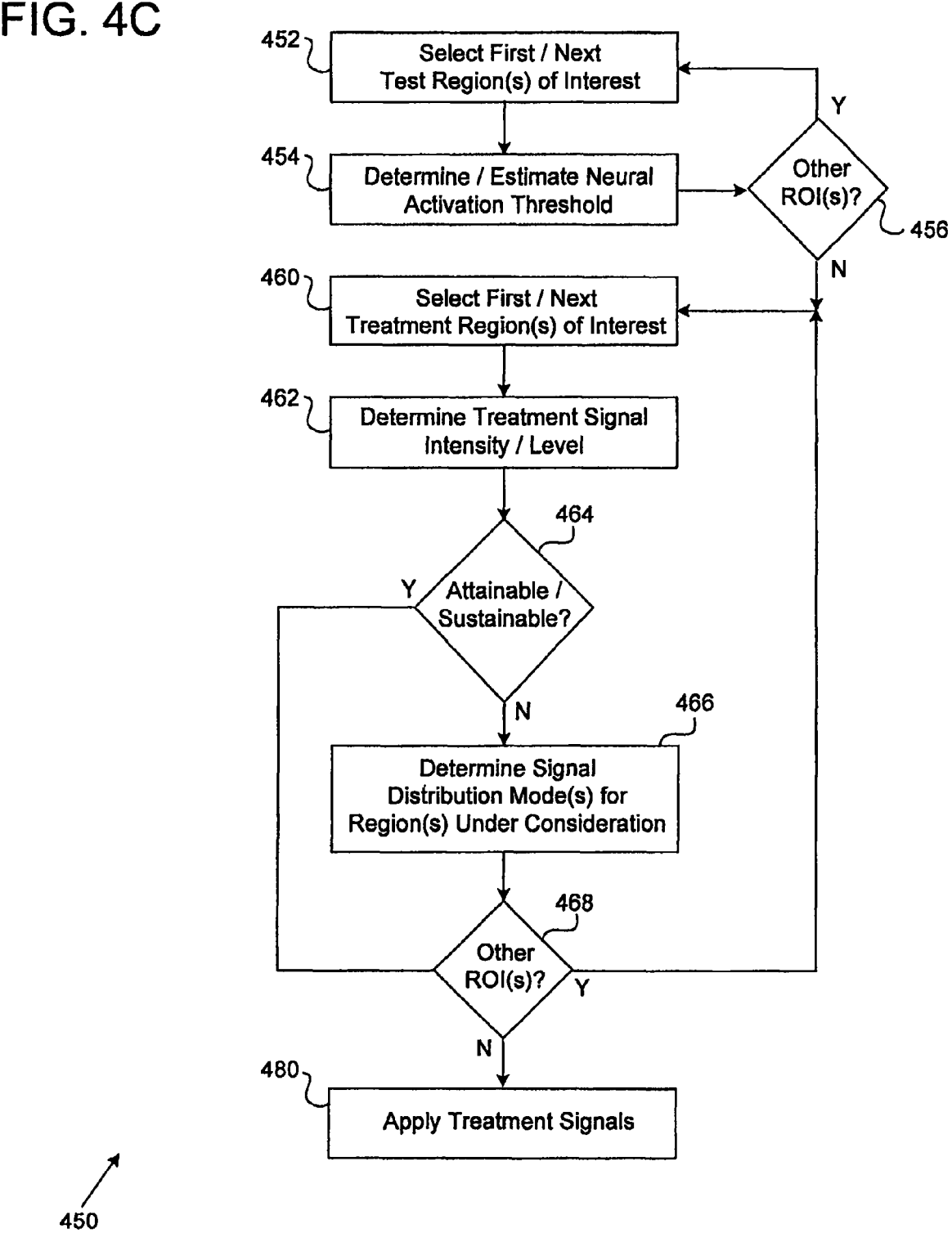
FIG. 4C is a flowchart illustrating a method in accordance with yet another embodiment of the invention.

FIG. 4C is a flowchart illustrating a method 450 in accordance with another embodiment of the invention. In one embodiment, the method 450 includes a first stage 452 of identifying or selecting at least one test site or region of interest. Test stimulation signals can be applied to the selected test region(s) at a second stage 454 to determine or estimate a neural activation threshold corresponding to the selected region(s). Determination of a neural activation threshold can involve the application of test signals to a single neural area (e.g., a portion of the primary motor cortex), or the simultaneous or sequential application of test signals to multiple neural areas (e.g., portions of the primary motor and premotor cortices). The method 450 further includes a third stage 456 of determining whether to consider one or more additional or other test regions. The method 450 returns to the first stage 452 if such is the case.

In a manner identical or analogous to that described above with reference to FIG. 2B, the determination of a given neural activation threshold at the second stage 454 can involve the application of stimulation signals to progressively smaller electrode subsets within or adjacent to a set of test regions under consideration until a desired effect or a patient response occurs, an upper signal limit is reached, or a smallest electrode subset (e.g., an electrode subset having a single electrode; or an electrode subset having one electrode positioned relative to a first neurofunctional area and another electrode positioned relative to another neurofunctional area) has been considered.

Different test regions can exhibit different neural activation thresholds. For example, a first threshold (e.g., a motor response evoked at approximately 9 mA) may be measured during the epidural application of first test stimulation signals to a first portion of the primary motor cortex using a given 1×3 row of electrodes within a 2×3 electrode array; and a second threshold (e.g., a motor or sensory response evoked at approximately 12 mA) may be measured during the epidural application of second test stimulation signals to the other 1×3 row of electrodes within this 2×3 array.

As another example, a first threshold (e.g., a motor response evoked at approximately 8 mA) may be measured during the epidural application of first test stimulation signals to a portion of the primary motor cortex; and a second threshold (e.g., a motor response evoked at approximately 4.5 mA) may be measured during the epidural application of second test stimulation signals to a portion of the ipsilateral premotor cortex. As a more specific example, a first threshold may be determined as a result of the application of first test stimulation signals to a first test region that includes a portion of the primary motor cortex or the somatosensory cortex in a brain hemisphere affected by neurologic damage (e.g., as a result of a stroke or traumatic brain injury); and a second threshold may be determined as a result of the application of second test stimulation signals to a second test region that includes a portion of the primary motor cortex or the premotor cortex in the opposite brain hemisphere. One or more measured neural activation thresholds can be stored in a memory or other computer readable medium, within the pulse generator and/or an external programming device 110.

The method 450 also includes a fourth stage 460 of selecting at least one treatment region of interest. Depending upon embodiment details, a set of treatment regions may be identical to, overlapping with, or different from the test region(s) considered at the first through third stages 452-456. The method 450 further includes a fifth stage 462 of determining or estimating a target treatment signal intensity or level for simultaneous application to the electrodes spanning the selected treatment region(s) of interest.

A target treatment signal intensity can be based upon one or more neural activation thresholds determined in association with the second stage 454. For example, if a motor threshold corresponding to a given 1×3 row of electrodes within a 2×3 electrode array is about 9 mA, then a target treatment signal intensity for this electrode row can be about 25%-75%, or about 50%, of 9 mA (e.g., 4.5 mA). If a motor threshold corresponding to the other 1×3 electrode row is about 12 mA, then a target treatment signal intensity for this 1×3 electrode row can be approximately 25%-75% of 12 mA (e.g., 6 mA, or 8 mA).

As another example, if a motor threshold determined at the second stage 454 is approximately equal to 9 mA, then a target treatment signal intensity directed toward stimulating a particular portion of the motor cortex may be between approximately 25%-75% of this motor threshold (e.g., 4.5 mA). Additionally or alternatively, a target treatment signal intensity for separately, simultaneously, or sequentially stimulating a portion of the somatosensory cortex or the SMA may be between approximately 10%-90% of this motor threshold (e.g., approximately 4 mA-8 mA).

As an additional example, if a first threshold corresponding to a first brain hemisphere equals approximately 14 mA and a second threshold corresponding to the second brain hemisphere equals approximately 8 mA, then a target treatment signal intensity directed toward the first brain hemisphere may be based upon a lowest or a highest threshold level (e.g., approximately 50% of the second hemisphere's threshold), or a mathematical function of the measured threshold levels (e.g., approximately 25%-75%, or about 50%, of an average of the measured threshold levels).

As yet another example, if a motor, sensation, or other threshold level measured in response to cortical stimulation alone equals approximately 9.5 mA, and a corresponding threshold level measured during the simultaneous application of cortical stimulation and DBS (e.g., directed toward a basal ganglia or thalamic neural population; or directed toward a portion of the cingulate gyrus, the amygdala, or the nucleus basalis), PNS (e.g., applied to a cranial nerve such as the vagal nerve), or SCS (e.g., applied proximate to a spinal column region that has been affected by neurologic damage, but which is least partially functional) equals approximately 6 mA, then a target treatment signal intensity for cortical stimulation alone or a combination of cortical plus other stimulation can be based upon one or both of these measured threshold levels (e.g., in a manner analogous to that described for the preceding example).

As still another example, if a working memory task or other cognitive activity (e.g., a reaction time) is affected by the application of a 6 mA test stimulation signal to a portion of the left DLPFC, then a target treatment signal intensity for the left DLPFC can be approximately 75%-95% (e.g., approximately 4.8 mA-5.4 mA) of such a cognitive threshold. Additionally or alternatively, a target treatment signal intensity for the right DLPFC and/or the OFC may be approximately 25%-95% (e.g., approximately 3 mA or 4 mA, or approximately 4.8 mA-5.4 mA) of this cognitive threshold.

One or more treatment regions of interest and/or target treatment signal intensities may be selected by a clinician or a patient (e.g., via an input device coupled to an appropriate type of external programming unit 110) based upon therapeutic efficacy and/or symptomatic severity at one or more times. For example, if symptomatic benefit or relief from a pain condition occurs in response to test stimulation signals applied to the cortex at approximately 6.5 mA; or test stimulation signals applied to a spinal column area at approximately 4.5 mA; and/or test stimulation signals concurrently or sequentially applied to the cortex and a spinal column area at approximately 3.5 mA, then a set of treatment regions and a target treatment signal level may be selected in response to clinician or patient input (e.g., via an appropriate type of external programming device 110) based upon previous, current, or expected future therapeutic efficacy (e.g., in response to a plateau or decline in therapeutic efficacy after a particular set of treatment regions have been stimulated for a particular number of days or weeks using a given set of stimulation parameters).

As an additional example, if symptomatic relief from phantom limb pain (PLP) occurs in response to test stimulation signals applied to portions of the motor or somatosensory cortex at approximately 4.0-6.0 mA, and symptomatic relief from post-traumatic stress disorder (PTSD) or an anxiety or panic disorder occurs in response to test stimulation signals applied to portions of the DLPFC at approximately 7.5 mA, then a clinician or the patient can select a set of treatment regions and/or a set of target treatment signal intensities based upon the severity of the symptoms associated with one or both disorders at any given time.

The method 450 also includes a sixth stage 464 of determining whether the target treatment signal intensity for the treatment region(s) under consideration is attainable or sustainable in view of stimulation device limitations. If the target treatment signal intensity is not achievable, the method 450 includes a seventh stage 466 of determining at least one signal distribution mode that facilitates the delivery of sufficiently intense treatment signals to smaller numbers of electrodes at any given time, in a manner analogous to that described above.

The method 450 additionally includes an eighth stage 468 of determining whether to consider the determination or definition of a treatment signal intensity for one or more other treatment regions of interest. If so, the method 450 returns to the fourth stage 460. Finally, the method 450 includes a ninth stage 480 of applying treatment stimulation signals to a set of treatment region(s), in accordance with one or more signal distribution modes that may have been defined at the method's the seventh stage 466.

From the foregoing, it will be appreciated that specific embodiments of the invention have been described herein for purposes of illustration, but that various modifications may be made without deviating from the spirit and scope of the invention. For example, particular methods do not need to apply the stimulation via the subset of electrodes after applying the current to a larger number of electrodes at approximately the maximum output of the pulse generator. The following examples provide still further representative embodiments.

The invention claimed is:

1. A method for providing electrical stimulation therapy to a cortex of a patient via a plurality of electrodes proximate to the cortex and a pulse generator implanted in the patient, the method comprising:
   determining whether a current density of an electrical field in the cortex applied via the plurality of electrodes is sufficient for a desired purpose;
   if the current density is not sufficient, then selecting a subset of the plurality of electrodes to produce a higher current density in the cortical area at or beneath the subset of the plurality of electrodes; and
   applying electrical current to the cortex through the subset of the plurality of electrodes thereby increasing the current density to achieve the desired therapy.

2. The method of claim 1 further comprising applying electrical current to the cortex via the plurality of electrodes at approximately a maximum output of the pulse generator, and wherein determining whether the current density is sufficient includes making an assessment that the current density is not sufficient when the electrical current via the plurality of electrodes does not induce a motor and/or a sensory response in the patient.

3. The method of claim 2 wherein the electrical current is initially applied to the subset of electrodes at an output less than the maximum output of the pulse generator, and the electrical current is subsequently applied to the subset of electrodes at increasing levels until a motor and/or sensory response is induced in the patient, whereby the current level inducing the response is identified as a suprathreshold current.

4. The method of claim 3, further comprises selecting a subthreshold current less than the suprathreshold current and applying the subthreshold current through the plurality of electrodes.

5. The method of claim 1 wherein the plurality of electrodes are mounted to a flexible substrate and define an electrode array configured to cover an area of the cortex, and wherein a maximum output of the pulse generator is not sufficient to provide the electrical stimulation therapy concurrently through the plurality of electrodes.

6. The method of claim 5 wherein applying the current through a subset of the plurality of the electrodes comprises applying electrical current to the cortex via a first electrode at approximately a maximum output of the pulse generator for a first time period and applying electrical current to the cortex via a second electrode at approximately a maximum output of the pulse generator for a second period of time.

7. The method of claim 5 wherein applying the current through a subset of the plurality of electrodes comprises applying electrical current to different electrodes at different times to provide a current density at individual electrodes greater than when the current was applied concurrently via the plurality of electrodes.

8. The method of claim 5 wherein applying the current through a subset of the plurality of electrodes comprises time multiplexing the current through a first subset of the plurality of electrodes and a second subset of the plurality of electrodes at different time periods.

9. The method of claim 5 wherein applying the current through a subset of the plurality of electrodes comprises frequency multiplexing the current through a first subset of the plurality of electrodes and a second subset of the plurality of electrodes.

10. A method for applying electrical current to a cortex of a patient via a pulse generator implanted in the patient, comprising:
    implanting an electrode array at least proximate to the cortex of the patient, the electrode array having a flexible support member and a plurality of electrodes mounted to the support member, and the electrode array being electrically coupled to the implanted pulse generator such that at least one first electrode can be operated independently of at least one second electrode;
    determining that an electrical current applied concurrently to the first electrode and the second electrode produces an electrical field in the cortex having a large area current density which is not sufficient to carry out an aspect of a cortical stimulation therapy for the patient;
    applying electrical current to the cortex via the first electrode for a first time period without applying electrical stimulation to the second electrode, wherein a first current density at the first electrode is higher than the large area current density; and
    applying electrical current to the cortex via the second electrode for a second time period without applying electrical stimulation to the first electrode, wherein a second current density at the second electrode is higher than the large area current density.

11. The method of claim 10 wherein the electrical current applied concurrently to the first and second electrodes is applied at approximately a maximum output of the implanted pulse generator.

12. The method of claim 10 wherein the plurality of electrodes are arranged to cover a large area of the cortex, and wherein a maximum output of the pulse generator is not sufficient to provide the electrical stimulation therapy concurrently through the plurality of electrodes.

13. The method of claim 10 wherein applying the current through the first electrode during the first time period and applying the current through the second electrode for the second time period comprises time multiplexing the current through the first and second electrodes.

14. The method of claim 10 wherein applying the current through the first electrode for the first time period and applying the current through the second electrode for the second time period comprises frequency multiplexing the current through the first and second electrodes.

15. A cortical stimulation system, comprising:
- an electrode array configured to be implanted at least proximate to the cortex, wherein the electrode array has a plurality of electrodes; and
- a pulse generator configured to be coupled to the electrode array to provide electrical signals to at least one of the electrodes, wherein the pulse generator comprises a controller having instructions that cause the pulse generator to (a) receive a determination of whether a current density of an electrical field in the cortex applied via the electrodes is sufficient for a desired purpose, (b) if the current density is not sufficient, then select a subset of the plurality of the electrodes, and (c) apply electrical current to the cortex through the subset of the plurality of the electrodes to produce a higher current density in the cortical area at or beneath the subset of the plurality of electrodes.

16. The system of claim 15, wherein the instructions of the controller further cause the pulse generator to (a) apply the electrical current to the cortex via the plurality of electrodes at approximately a maximum output of the pulse generator, and (b) receive a determination of whether the current density is sufficient by sensing neural activity and making an assessment that the current density is not sufficient when the electrical current via the plurality of electrodes does not induce a sufficient measurable response associated with neural activity in the patient.

17. The system of claim 16 wherein the instructions of the controller further cause the pulse generator to (a) initially apply the electrical current to the subset of electrodes at an output less than the maximum output of the pulse generator, and (b) subsequently apply the electrical current to the subset of electrodes at increasing levels until a motor and/or sensory response is induced in the patient, whereby the current level inducing the response is identified as a suprathreshold current.

18. The system of claim 17, wherein the instructions of the controller further cause the pulse generator to (a) select a subthreshold current less than the suprathreshold current and (b) apply the subthreshold current through the plurality of electrodes.

19. The method of claim 18 wherein the subthreshold stimulation current is 25%-75% of the suprathreshold current.

20. The method of claim 18 wherein the subthreshold stimulation current is approximately 40%-60% of the suprathreshold current.

21. The system of claim 15 wherein the electrode array further comprises a flexible substrate and the electrodes are surface electrodes carried by the flexible substrate in an arrangement configured to cover an area of the cortex, and wherein a maximum output of the pulse generator is not sufficient to provide the electrical stimulation therapy concurrently through the plurality of electrodes.

22. The system of claim 21 wherein the instructions of the controller cause the pulse generator to apply the current through a subset of the plurality of the electrodes by (a) applying electrical current to the cortex via a first electrode at approximately a maximum output of the pulse generator for a first time period and (b) applying electrical current to the cortex via a second electrode at approximately a maximum output of the pulse generator for a second period of time.

23. The system of claim 21 wherein the instructions of the controller cause the pulse generator to apply the current through a subset of the plurality of electrodes by applying electrical current to different electrodes at different times to provide a current density at individual electrodes greater than when the current was applied concurrently via the plurality of electrodes.

24. The system of claim 21 wherein the instructions of the controller cause the pulse generator to apply the current through a subset of the plurality of electrodes by time multiplexing the current through a first subset of the plurality of electrodes and a second subset of the plurality of electrodes at different time periods.

25. The system of claim 21 wherein the instructions of the controller cause the pulse generator to apply the current through a subset of the plurality of electrodes by frequency multiplexing the current through a first subset of the plurality of electrodes and a second subset of the plurality of electrodes.

* * * * *